US 7,988,637 B2
Aug. 2, 2011

(12) United States Patent
Diab

(54) PLETHYSMOGRAPH PULSE RECOGNITION PROCESSOR

(75) Inventor: Mohamed K. Diab, Mission Viejo, CA (US)

(73) Assignee: Masimo Corporation, Irvine, CA (US)

( * ) Notice: Subject to any disclaimer, the term of this patent is extended or adjusted under 35 U.S.C. 154(b) by 1459 days.

(21) Appl. No.: 11/418,328

(22) Filed: May 3, 2006

(65) Prior Publication Data

US 2006/0206021 A1    Sep. 14, 2006

Related U.S. Application Data

(63) Continuation of application No. 10/974,095, filed on Oct. 27, 2004, now Pat. No. 7,044,918, which is a continuation of application No. 10/267,446, filed on Oct. 8, 2002, now Pat. No. 6,816,741, which is a continuation of application No. 09/471,510, filed on Dec. 23, 1999, now Pat. No. 6,463,311.

(60) Provisional application No. 60/114,127, filed on Dec. 30, 1998.

(51) Int. Cl.
  *A61B 5/02* (2006.01)
  *A61B 6/00* (2006.01)
(52) U.S. Cl. .......... 600/500; 600/479; 600/476
(58) Field of Classification Search .......... 600/500–504, 600/483, 481, 513
See application file for complete search history.

(56) References Cited

U.S. PATENT DOCUMENTS

| | | | |
|---|---|---|---|
| 4,295,471 A | 10/1981 | Kaspari | |
| 4,802,486 A | 2/1989 | Goodman et al. | |
| 4,938,228 A * | 7/1990 | Righter et al. | 600/503 |
| 4,960,126 A | 10/1990 | Conlon et al. | |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,243,992 A | 9/1993 | Eckerle et al. | |
| 5,274,548 A | 12/1993 | Bernard et al. | |
| 5,299,120 A * | 3/1994 | Kaestle | 600/310 |
| 5,337,744 A | 8/1994 | Branigan | |
| 5,349,519 A * | 9/1994 | Kaestle | 600/500 |
| 5,365,934 A | 11/1994 | Leon et al. | |
| D353,195 S | 12/1994 | Savage et al. | |
| D353,196 S | 12/1994 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |

(Continued)

FOREIGN PATENT DOCUMENTS

WO    WO 94/27492    8/1994

OTHER PUBLICATIONS

European Search Report mailed by the European Patent Office on Apr. 25, 2008 in 2 pages.
International Search Report, May 2, 2000.
Christ, F., et al., *"Time Discrete Near Infrared Photoplethysmography (NIRP) for Non-Invasive Investigation of Volume Pulse in Man,"* European Journal of Medical Research, pp. 237-243, Feb. 22, 1996.

*Primary Examiner* — Charles A Marmor, II
*Assistant Examiner* — Navin Natnithithadha
(74) *Attorney, Agent, or Firm* — Knobbe, Martens, Olson & Bear LLP

(57) ABSTRACT

A time domain rule-based processor provides recognition of individual pulses in a pulse oximeter-derived waveform.

12 Claims, 19 Drawing Sheets

U.S. PATENT DOCUMENTS

| | | | |
|---|---|---|---|
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,535,753 A * | 7/1996 | Petrucelli et al. | 600/485 |
| 5,553,615 A | 9/1996 | Carim et al. | |
| 5,562,002 A | 10/1996 | Lalin | |
| 5,590,649 A | 1/1997 | Caro et al. | |
| 5,602,924 A | 2/1997 | Durand et al. | |
| 5,623,937 A * | 4/1997 | Sasaki | 600/521 |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,647,369 A * | 7/1997 | Petrucelli et al. | 600/526 |
| 5,651,370 A | 7/1997 | Hersh et al. | |
| 5,682,898 A | 11/1997 | Aung et al. | |
| 5,685,299 A | 11/1997 | Diab et al. | |
| D393,830 S | 4/1998 | Tobler et al. | |
| 5,738,104 A * | 4/1998 | Lo et al. | 600/521 |
| 5,743,262 A | 4/1998 | Lepper, Jr. et al. | |
| 5,755,226 A | 5/1998 | Carim et al. | |
| 5,758,644 A | 6/1998 | Diab et al. | |
| 5,760,910 A | 6/1998 | Lepper, Jr. et al. | |
| 5,766,127 A * | 6/1998 | Pologe et al. | 600/310 |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,853,364 A | 12/1998 | Baker et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,101,410 A * | 8/2000 | Panescu et al. | 600/522 |
| 6,110,522 A | 8/2000 | Lepper, Jr. et al. | |
| 6,122,535 A | 9/2000 | Kaestle et al. | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,236,872 B1 | 5/2001 | Diab et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,312,387 B1 * | 11/2001 | Nissila et al. | 600/500 |
| 6,321,100 B1 | 11/2001 | Parker | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,393,311 B1 | 5/2002 | Edgar, Jr. et al. | |
| 6,397,091 B2 | 5/2002 | Diab et al. | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,575,915 B2 * | 6/2003 | Nissila et al. | 600/500 |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kianl et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,585 B1 | 4/2004 | Parker | |
| 6,725,075 B2 | 4/2004 | Al-Ali | |
| 6,735,459 B2 | 5/2004 | Parker | |
| 6,745,060 B2 | 6/2004 | Diab et al. | |
| 6,760,607 B2 | 7/2004 | Al-Ali | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |
| 6,898,452 B2 | 5/2005 | Al-Ali et al. | |
| 6,920,345 B2 | 7/2005 | Al-Ali et al. | |
| 6,931,268 B1 | 8/2005 | Kiani-Azarbayjany et al. | |
| 6,934,570 B2 | 8/2005 | Kiani et al. | |
| 6,939,305 B2 | 9/2005 | Flaherty et al. | |
| 6,943,348 B1 | 9/2005 | Coffin, IV | |
| 6,950,687 B2 | 9/2005 | Al-Ali | |
| 6,961,598 B2 | 11/2005 | Diab | |
| 6,970,792 B1 | 11/2005 | Diab | |
| 6,979,812 B2 | 12/2005 | Al-Ali | |
| 6,985,764 B2 | 1/2006 | Mason et al. | |
| 6,993,371 B2 | 1/2006 | Kiani et al. | |
| 6,996,427 B2 | 2/2006 | Ali et al. | |
| 6,999,904 B2 | 2/2006 | Weber et al. | |
| 7,003,338 B2 | 2/2006 | Weber et al. | |
| 7,003,339 B2 | 2/2006 | Diab et al. | |
| 7,015,451 B2 | 3/2006 | Dalke et al. | |
| 7,024,233 B2 | 4/2006 | Al et al. | |
| 7,027,849 B2 | 4/2006 | Al-Ali | |
| 7,030,749 B2 | 4/2006 | Al-Ali | |
| 7,039,449 B2 | 5/2006 | Al-Ali | |
| 7,044,918 B2 * | 5/2006 | Diab | 600/502 |
| 7,225,013 B2 * | 5/2007 | Geva et al. | 600/513 |

* cited by examiner

US 7,988,637 B2

PLETHYSMOGRAPH PULSE RECOGNITION PROCESSOR

REFERENCE TO RELATED APPLICATION

The present application claims priority benefit under 35 U.S.C. §120 to, and is a continuation of U.S. patent application Ser. No. 10/974,095, filed Oct. 27, 2004, entitled "Plethysmograph Pulse Recognition Processor," now U.S. Pat. No. 7,044,918, which is a continuation of U.S. patent application Ser. No. 10/267,446, filed Oct. 8, 2002, entitled "Plethysmograph Pulse Recognition Processor," now U.S. Pat. No. 6,816,741, which is a continuation of U.S. patent application Ser. No. 09/471,510, filed Dec. 23, 1999, entitled "Plethysmograph Pulse Recognition Processor," now U.S. Pat. No. 6,463,311, which claims priority benefit under 35 U.S.C. §119(e) from U.S. Provisional Application No. 60/114,127, filed Dec. 30, 1998, entitled "Plethysmograph Pulse Recognition Processor." The present application also incorporates the foregoing utility disclosures herein by reference.

BACKGROUND OF THE INVENTION

Oximetry is the measurement of the oxygen status of blood. Early detection of low blood oxygen is critical in the medical field, for example in critical care and surgical applications, because an insufficient supply of oxygen can result in brain damage and death in a matter of minutes. Pulse oximetry is a widely accepted noninvasive procedure for measuring the oxygen saturation level of arterial blood, an indicator of oxygen supply. A pulse oximeter typically provides a numerical readout of the patient's oxygen saturation, a numerical readout of pulse rate, and an audible indicator or "beep" that occurs at each pulse.

A pulse oximetry system consists of a sensor attached to a patient, a monitor, and a cable connecting the sensor and monitor. Conventionally, a pulse oximetry sensor has both red and infrared (IR) light-emitting diode (LED) emitters and a photodiode detector. The sensor is typically attached to an adult patient's finger or an infant patient's foot. For a finger, the sensor is configured so that the emitters project light through the fingernail and into the blood vessels and capillaries underneath. The photodiode is positioned at the fingertip opposite the fingernail so as to detect the LED emitted light as it emerges from the finger tissues.

The pulse oximetry monitor (pulse oximeter) determines oxygen saturation by computing the differential absorption by arterial blood of the two wavelengths emitted by the sensor. The pulse oximeter alternately activates the sensor LED emitters and reads the resulting current generated by the photodiode detector. This current is proportional to the intensity of the detected light. The pulse oximeter calculates a ratio of detected red and infrared intensities, and an arterial oxygen saturation value is empirically determined based on the ratio obtained. The pulse oximeter contains circuitry for controlling the sensor, processing the sensor signals and displaying the patient's oxygen saturation and pulse rate. In addition, a pulse oximeter may display the patient's plethysmograph waveform, which is a visualization of blood volume change in the illuminated tissue caused by arterial blood flow over time. A pulse oximeter is described in U.S. Pat. No. 5,632,272 assigned to the assignee of the present invention.

SUMMARY OF THE INVENTION

FIG. 1 illustrates the standard plethysmograph waveform 100, which can be derived from a pulse oximeter. The waveform 100 is a display of blood volume, shown along the y-axis 110, over time, shown along the x-axis 120. The shape of the plethysmograph waveform 100 is a function of heart stroke volume, pressure gradient, arterial elasticity and peripheral resistance. The ideal waveform 100 displays a broad peripheral flow curve, with a short, steep inflow phase 130 followed by a 3 to 4 times longer outflow phase 140. The inflow phase 130 is the result of tissue distention by the rapid blood volume inflow during ventricular systole. During the outflow phase 140, blood flow continues into the vascular bed during diastole. The end diastolic baseline 150 indicates the minimum basal tissue perfusion. During the outflow phase 140 is a dicrotic notch 160, the nature of which is disputed. Classically, the dicrotic notch 160 is attributed to closure of the aortic valve at the end of ventricular systole. However, it may also be the result of reflection from the periphery of an initial, fast propagating, pressure pulse that occurs upon the opening of the aortic valve and that precedes the arterial flow wave. A double dicrotic notch can sometimes be observed, although its explanation is obscure, possibly the result of reflections reaching the sensor at different times.

FIG. 2 is a graph 200 illustrating a compartmental model of the absorption of light at a tissue site illuminated by a pulse oximetry sensor. The graph 200 has a y-axis 210 representing the total amount of light absorbed by the tissue site, with time shown along an x-axis 220. The total absorption is represented by layers, including the static absorption layers due to tissue 230, venous blood 240 and a baseline of arterial blood 250. Also shown is a variable absorption layer due to the pulse-added volume of arterial blood 260. The profile 270 of the pulse-added arterial blood 260 is seen as the plethysmograph waveform 100 depicted in FIG. 1.

FIG. 3 illustrates the photo-plethysmograph intensity signal 300 detected by a pulse oximeter sensor. A pulse oximeter does not directly detect absorption and, hence, does not directly measure the standard plethysmograph waveform 100 (FIG. 1). However, the standard plethysmograph can be derived by observing that the detected intensity signal 300 is merely an out of phase version of the absorption profile 270. That is, the peak detected intensity 372 occurs at minimum absorption 272 (FIG. 2), and the minimum detected intensity 374 occurs at maximum absorption 274 (FIG. 2). Further, a rapid rise in absorption 276 (FIG. 2) during the inflow phase of the plethysmograph is reflected in a rapid decline 376 in intensity, and the gradual decline 278 (FIG. 2) in absorption during the outflow phase of the plethysmograph is reflected in a gradual increase 378 in detected intensity.

In addition to blood oxygen saturation, a desired pulse oximetry parameter is the rate at which the heart is beating, i.e. the pulse rate. At first glance, it seems that it is an easy task to determine pulse rate from the red and infrared plethysmograph waveforms described above. However, this task is complicated, even under ideal conditions, by the variety of physiological plethysmographic waveforms. Further, plethysmographic waveforms are often corrupted by noise, including motion artifact, as described in U.S. Pat. No. 2,632,272 cited above. Plethysmograph pulse recognition, especially in the presence of motion artifact and other noise sources, is a useful component for determining pulse rate and also for providing a visual or audible indication of pulse occurrence.

In one aspect of the pulse recognition processor according to the present invention, information regarding pulses within an input plethysmograph waveform is provided at a processor output. The processor has a candidate pulse portion that determines a plurality of potential pulses within the input waveform. A physiological model portion of the processor then determines the physiologically acceptable ones of these potential pulses. The processor may further provide statistics regarding the acceptable pulses. One statistic is pulse density, which is the ratio of the period of acceptable pulses to the duration of an input waveform segment.

The candidate pulse portion has a series of components that remove from consideration as potential pulses those waveform portions that do not correspond to an idealized triangular waveform. This processing removes irrelevant waveform features such as the characteristic dicrotic notch and those caused by noise or motion artifact. The candidate pulse portion provides an output having indices that identify potential pulses relative to the peaks and valleys of this triangular waveform.

The physiological model portion of the processor has a series of components that discard potential pulses that do not compare to a physiologically acceptable pulse. The first component of the model portion extracts features of the potential pulses, including pulse starting point, pulse period, and pulse signal strength. These features are compared against various checks, including checks for pulses that have a period below a predetermined threshold, that are asymmetric, that have a descending trend that is generally slower that a subsequent ascending trend, that do not sufficiently comply with an empirical relationship between pulse rate and pulse signal strength, and that have a signal strength that differs from a short-term average signal strength by greater than a predetermined amount.

In another aspect of the present invention, a pulse recognition method includes the steps of identifying a plurality of potential pulses in an input waveform and comparing the potential pulses to a physiological pulse model to derive at least one physiologically acceptable pulse. A further step of generating statistics for acceptable pulses may also be included. The generating step includes the steps of determining a total period of acceptable pulses and calculating a ratio of this total period to a duration of an input waveform segment to derive a pulse density value. The comparing step includes the steps of extracting pulse features from potential pulses and checking the extracted features against pulse criteria.

Yet another aspect of the current invention is a pulse recognition processor having a candidate pulse means for identifying potential pulses in an input waveform and providing a triangular waveform output. The processor also has a plethysmograph model means for determining physiologically acceptable pulses in the triangular waveform output and providing as a pulse output the indices of acceptable pulses. The pulse recognition processor may further have a pulse statistics means for determining cumulative pulse characteristics from said pulse output.

BRIEF DESCRIPTION OF THE DRAWINGS

The present invention will be described in detail below in connection with the following drawing figures in which.

DETAILED DESCRIPTION OF THE PREFERRED EMBODIMENTS

Figure 4:
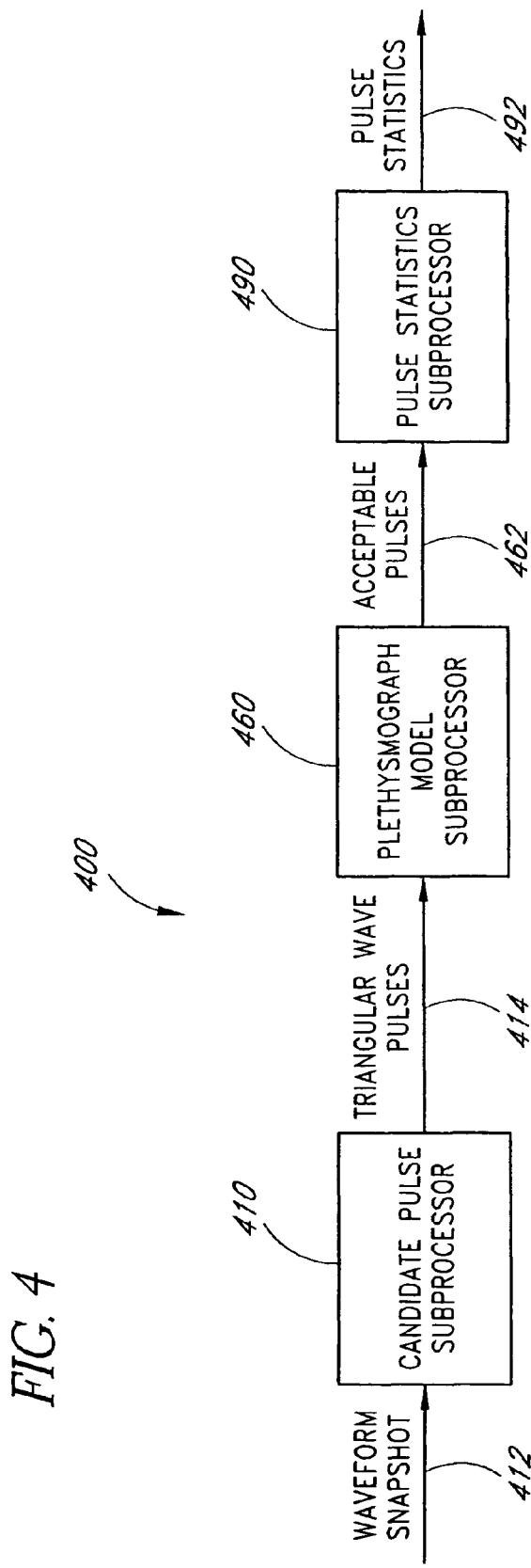
FIG. 4 is a block diagram of the plethysmograph pulse recognition processor according to the present invention.

FIG. 4 illustrates the plethysmograph pulse recognition processor 400 according to the present invention. The pulse processor 400 has three subprocessors, a candidate pulse subprocessor 410, a plethysmograph model subprocessor 460, and a pulse statistics subprocessor 490. The candidate pulse subprocessor 410 applies various waveform criteria or "edge checks" to find candidate pulses in an input waveform "snapshot" 412. In a particular embodiment, the snapshot is 400 samples of a detected intensity plethysmograph taken at a 62.5 Hz sampling rate. This snapshot represents a 6.4 second waveform segment. The output 414 of the candidate pulse subprocessor 410 is peaks and valleys of the input waveform segment representing a triangular wave model of identified candidate pulses. The candidate pulse output 414 is input to the plethysmograph model subprocessor 460, which compares these candidate pulses to an internal model for physiological pulses. The output 462 of the plethysmograph model subprocessor 460 is physiologically acceptable pulses. The acceptable pulse output 462 is input to the pulse statistics subprocessor. The output 492 of the pulse statistics subprocessor is statistics regarding acceptable pulses, including mean pulse period and pulse density, as described below.

Figure 1:
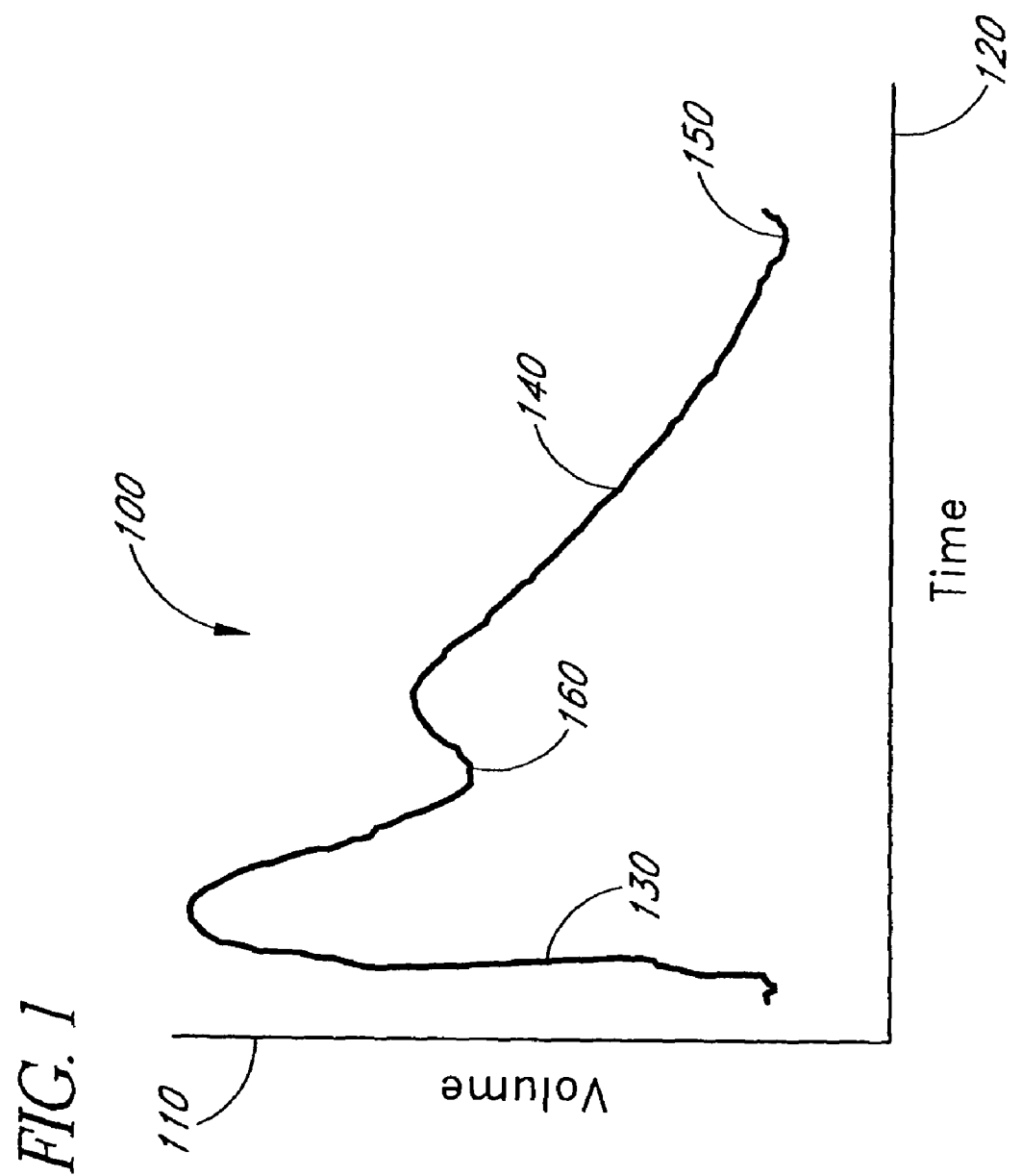
FIG. 1 is a graph illustrating a single pulse of a plethysmograph waveform.
Figure 2:
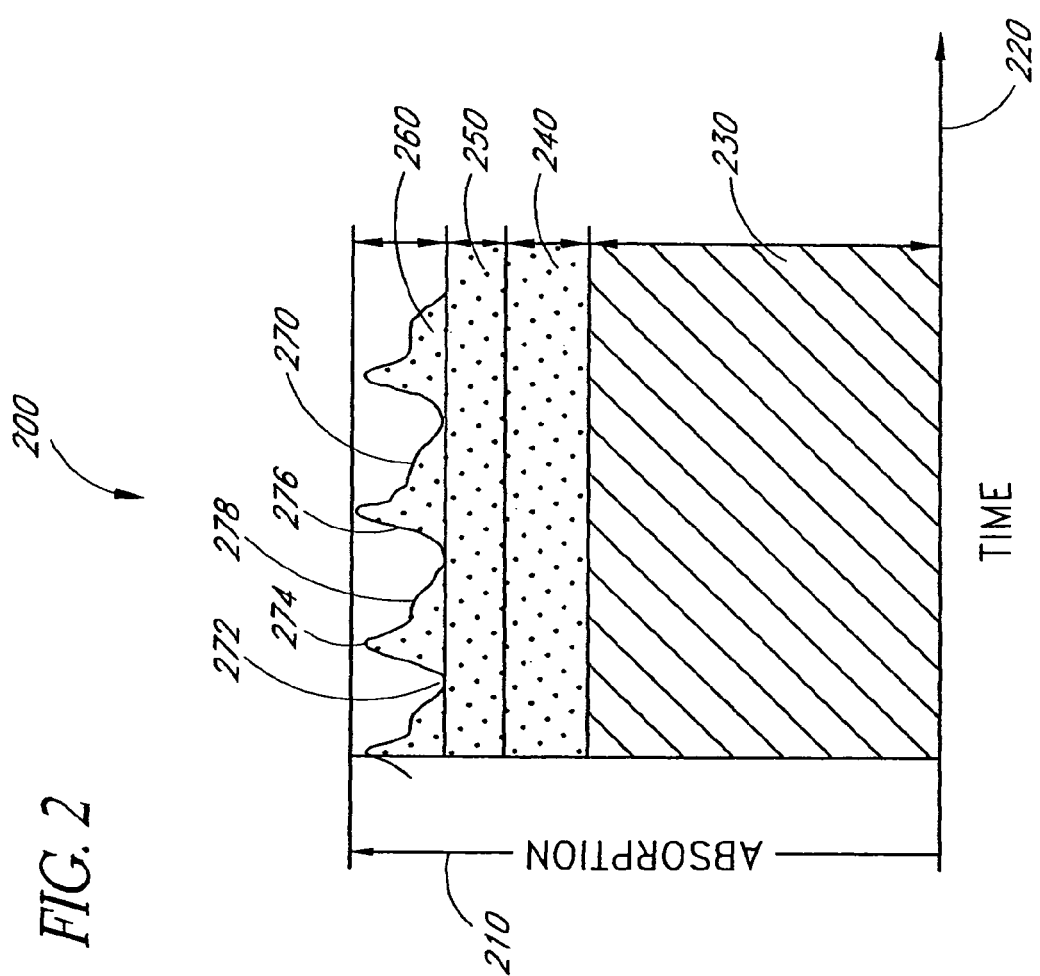
FIG. 2 is a graph illustrating the absorption contribution of various blood and tissue components.
Figure 3:
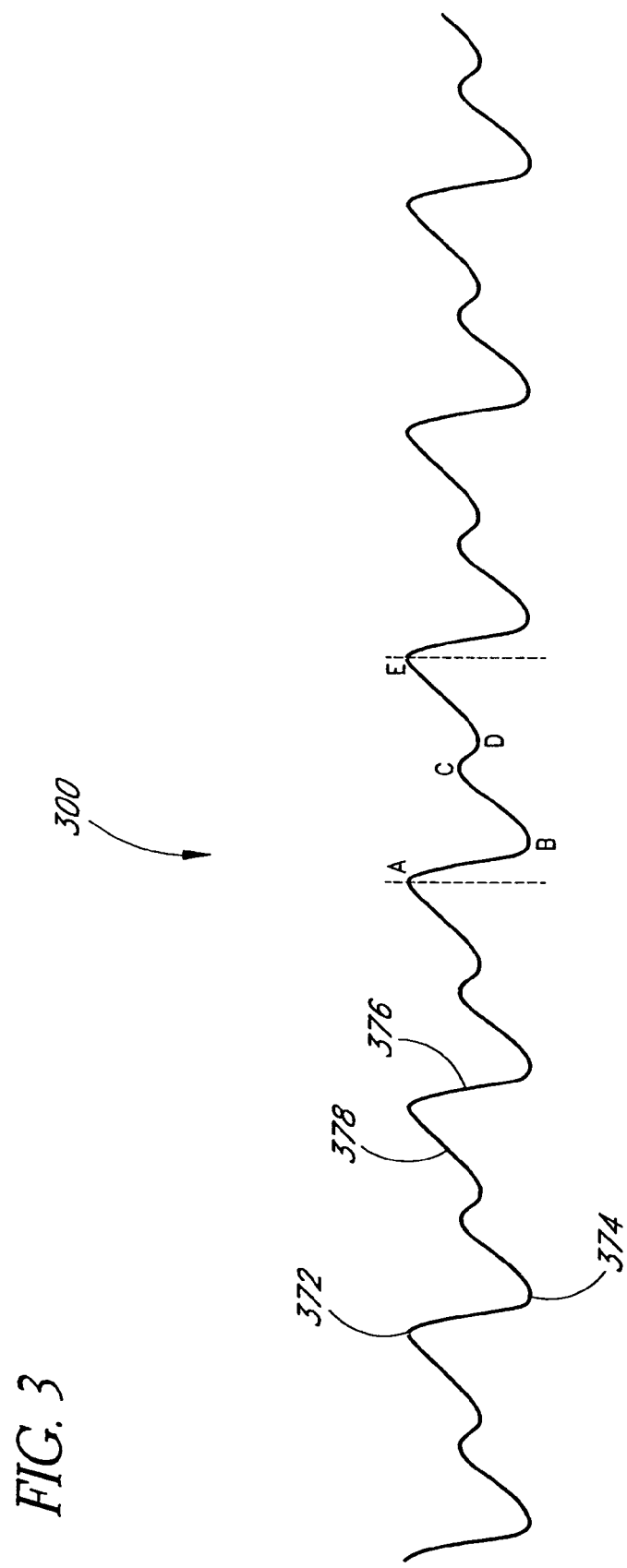
FIG. 3 is a graph illustrating an intensity "plethysmograph" pulse oximetry waveform.
Figure 5:
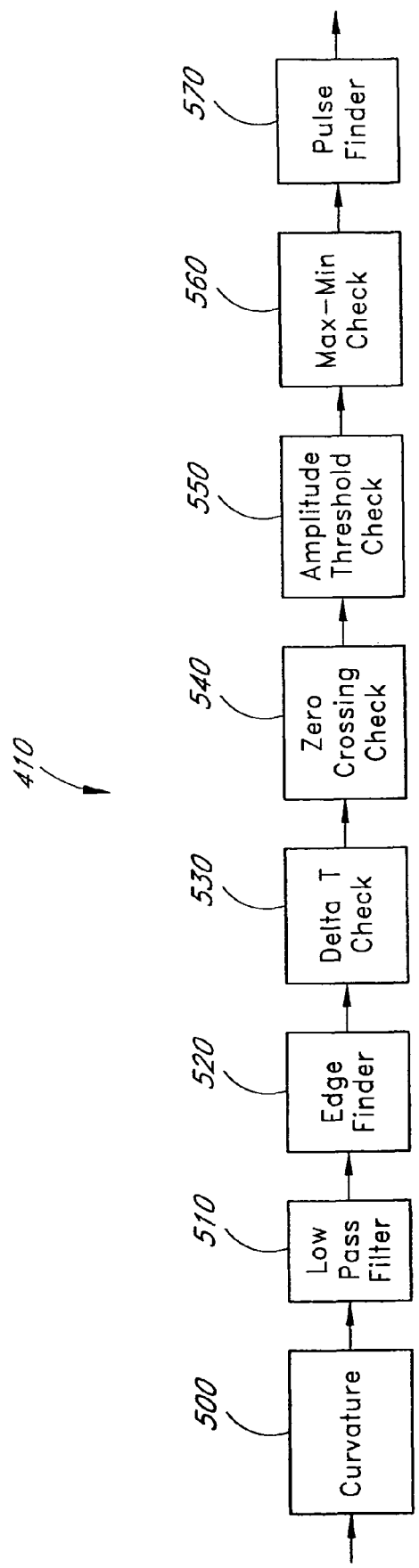
FIG. 5 is a block diagram of the candidate pulse finding subprocessor portion of the present invention.

FIG. 5 illustrates the components of the candidate pulse subprocessor 410. This subprocessor removes waveform features that do not correspond to an idealized triangular waveform, including the characteristic dicrotic notch. For example, as shown in FIG. 3, the candidate pulse component must identify points ABE, discarding points CD. The candidate pulse subprocessor 410 first identifies "edges" within the input waveform segment. An edge is defined as a segment that connects a peak and subsequent valley of the filtered waveform signal. The candidate pulse processor 410 then discards edges that do not meet certain conditions.

As shown in FIG. 5, the candidate pulse subprocessor has curvature 500, low-pass filter 510 (in one embodiment) and edge finder 520 components that identify edges. In one embodiment, the curvature component 510 is implemented by convolving the waveform with the kernel [1,−2,1]. In one embodiment, instead of a low-pass filter 510, a band-pass filter can be used. For a kernel size of n, this can be represented as follows:

$$y_k = w y_{k-1} + u_k \quad (1)$$

where $u_k$ is the kth input sample and $y_k$ is the kth output sample and w is a fixed weight that determines the amount of filter feedback. The edge finder 520 identifies the peaks and subsequent valleys of the output of the filter 510.

Figure 6:
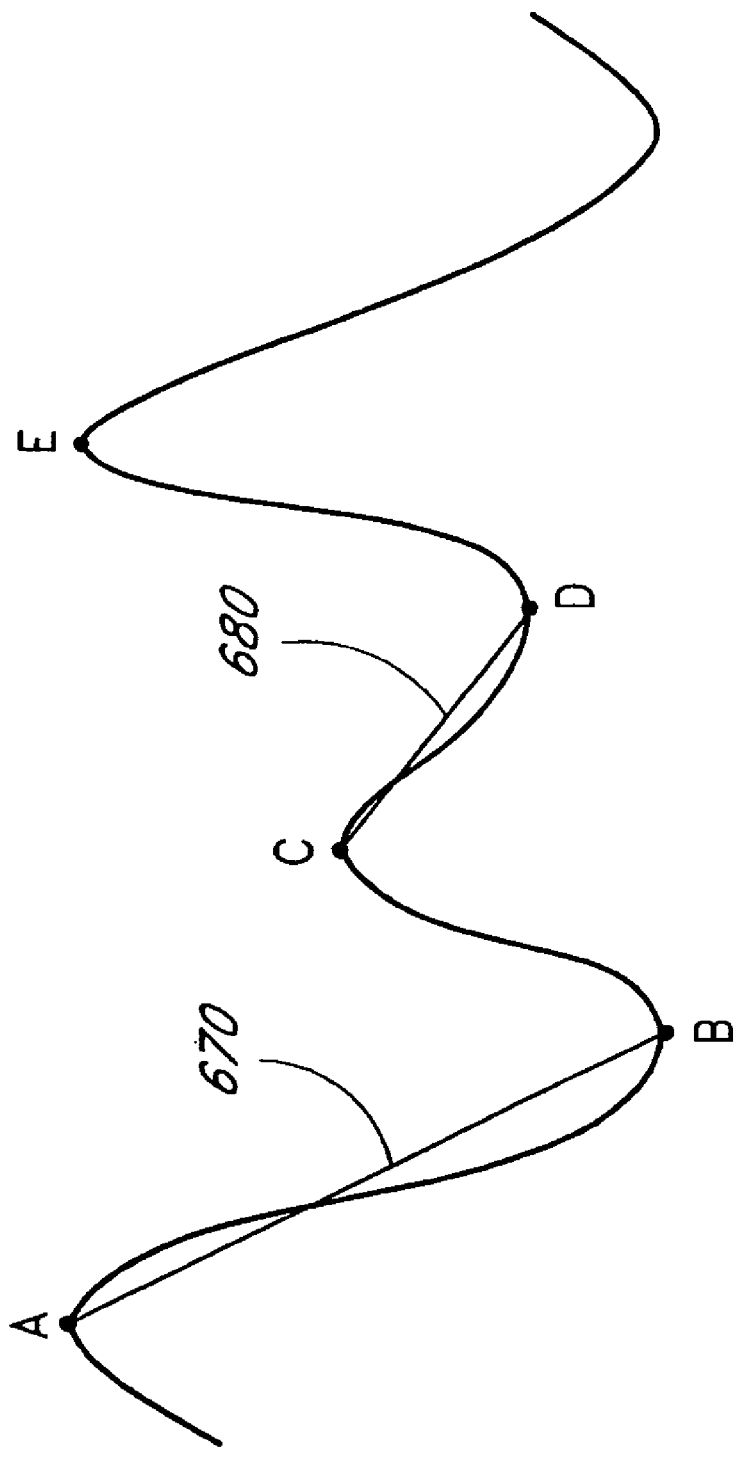
FIG. 6 is a graph illustrating the filtered, curvature of a plethysmograph pulse and the associated edges.

FIG. 6 illustrates the results of the curvature 500, filter 510 and edge finder 520 components applied to a couple waveform pulses 610. The processed waveform 660 has peaks A and C and corresponding valleys B and D. There are two edges, a first edge is represented by a line segment 670 connecting A and B. A second edge is represented by a line segment 680 connecting C and D.

As shown in FIG. 5, the candidate pulse portion also has delta T 530, zero crossing 540, amplitude threshold 550 and max-min 560 checks that eliminate certain of the identified edges. The delta T check 530 discards all the edges having a distance between end points that do not fall within a fixed interval. This is designed to eliminate pulse-like portions of the input waveform that are either too slow or too quick to be physiological pulses. In a particular embodiment, the interval is between 5 and 30 samples at the 62.5 Hz sampling rate, or 80-480 msec. That is, edges less than 80 msec. or greater than 480 msec. in length are eliminated.

Figure 7:
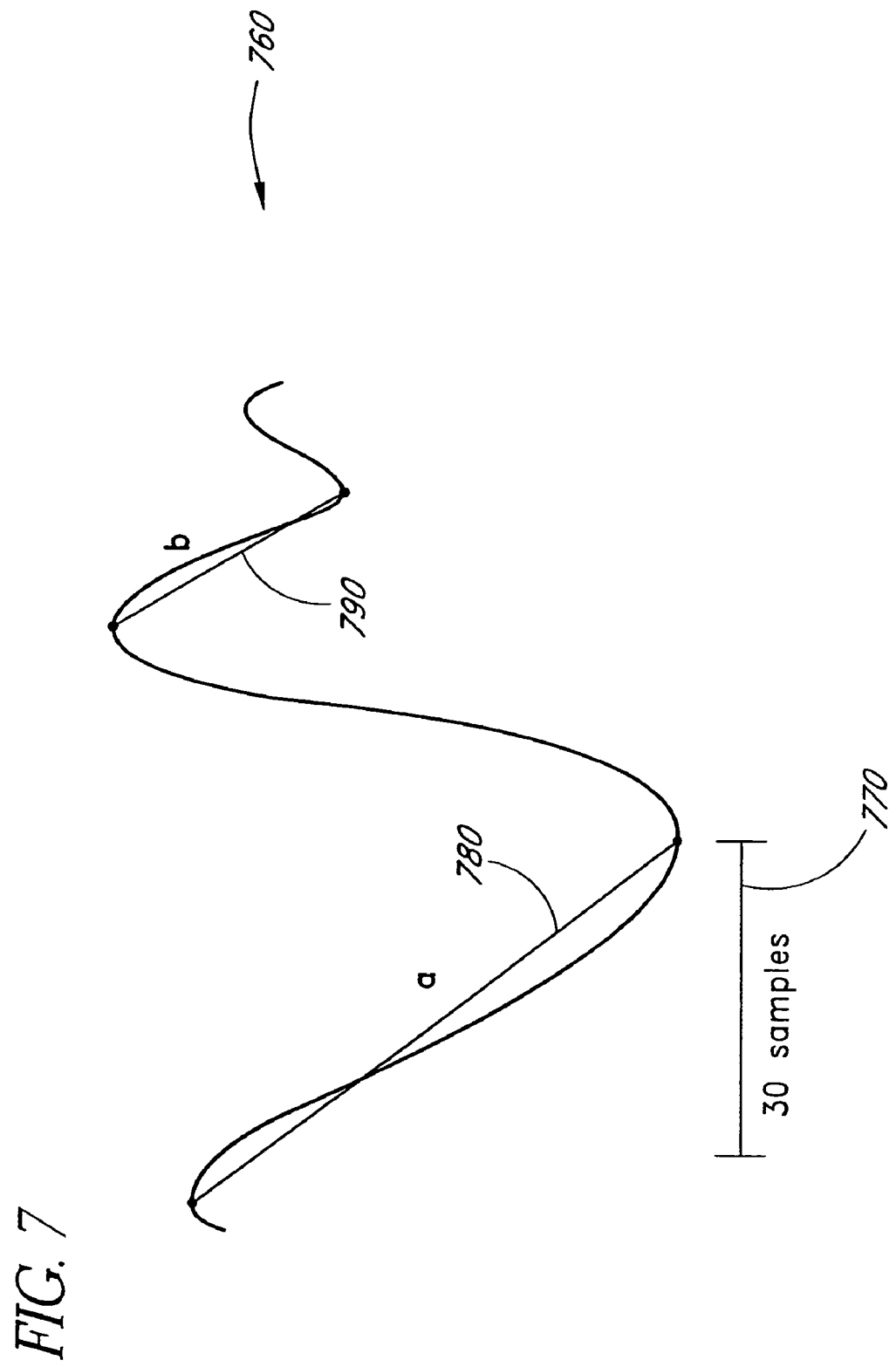
FIG. 7 is a graph illustrating the delta T check on the edges.

FIG. 7 illustrates the delta T check 530 (FIG. 5) described above. Shown is the processed waveform 760, edge a 780 and edge b 790, along with a maximum acceptable edge length interval 770 for comparison. In this example, edge a 780, which is 35 samples in length, would be eliminated as exceeding in length the maximum acceptable interval 770 of 30 samples. By contrast, edge b 790, which is 25 samples in length, would be accepted.

Also shown in FIG. 5, the zero crossing check 540 eliminates all edges that do not cross zero. The zero crossing check eliminates small curvature changes in the input waveform segment, i.e. small bumps that are not peaks and valleys.

Figure 8:
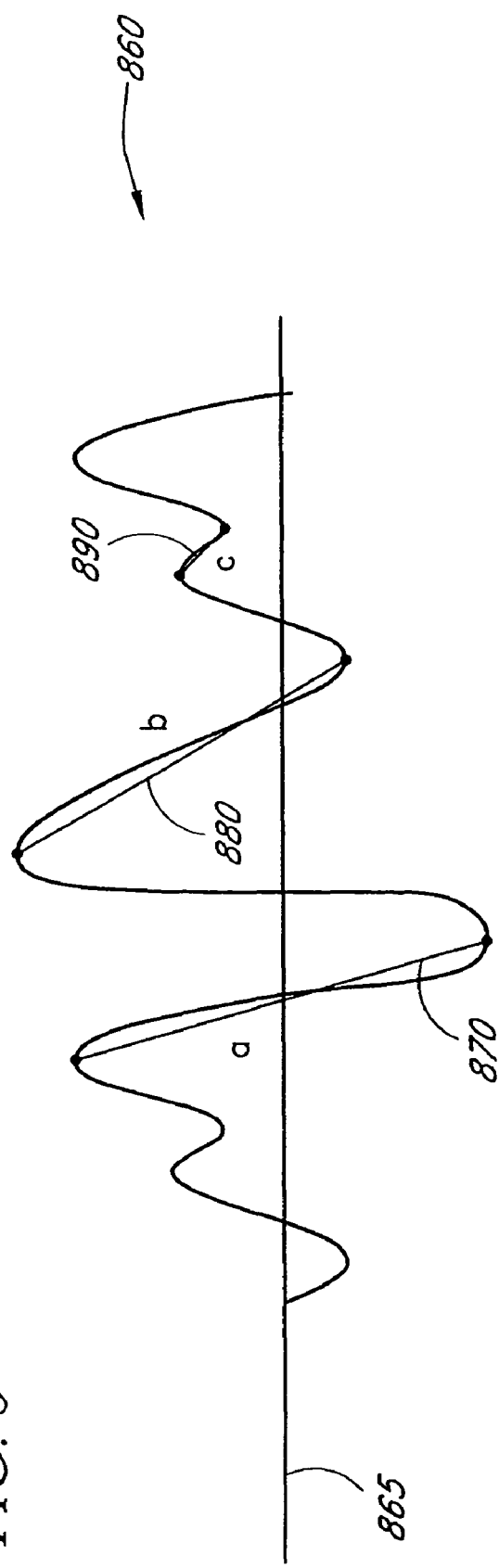
FIG. 8 is a graph illustrating the zero-crossing check on the edges.

FIG. 8 illustrates the effect of the zero crossing check 540 (FIG. 5). Shown is the processed waveform 860. Edge a 870, edge b 880 and edge c 890 are shown relative to the zero line 865 for the processed waveform 860. In this example, edges a 870 and edge b 880 are accepted, but edge c 890 is eliminated because it does not cross the zero line 865.

Shown in FIG. 5, the amplitude threshold check 550 is designed to remove larger "bumps" than the zero crossing check 540, such as dicrotic notches. This is done by comparing the right extreme (valley) of each edge within a fixed-length window to a threshold based on a fixed percentage of the minimum within that window. If the valley is not sufficiently deep, the edge is rejected. In a particular embodiment, the window size is set at 50 samples for neonates and 100 samples for adults in order accommodate the slower pulse rate of an adult. Also, a threshold of 60% of the minimum is used.

Figure 9:
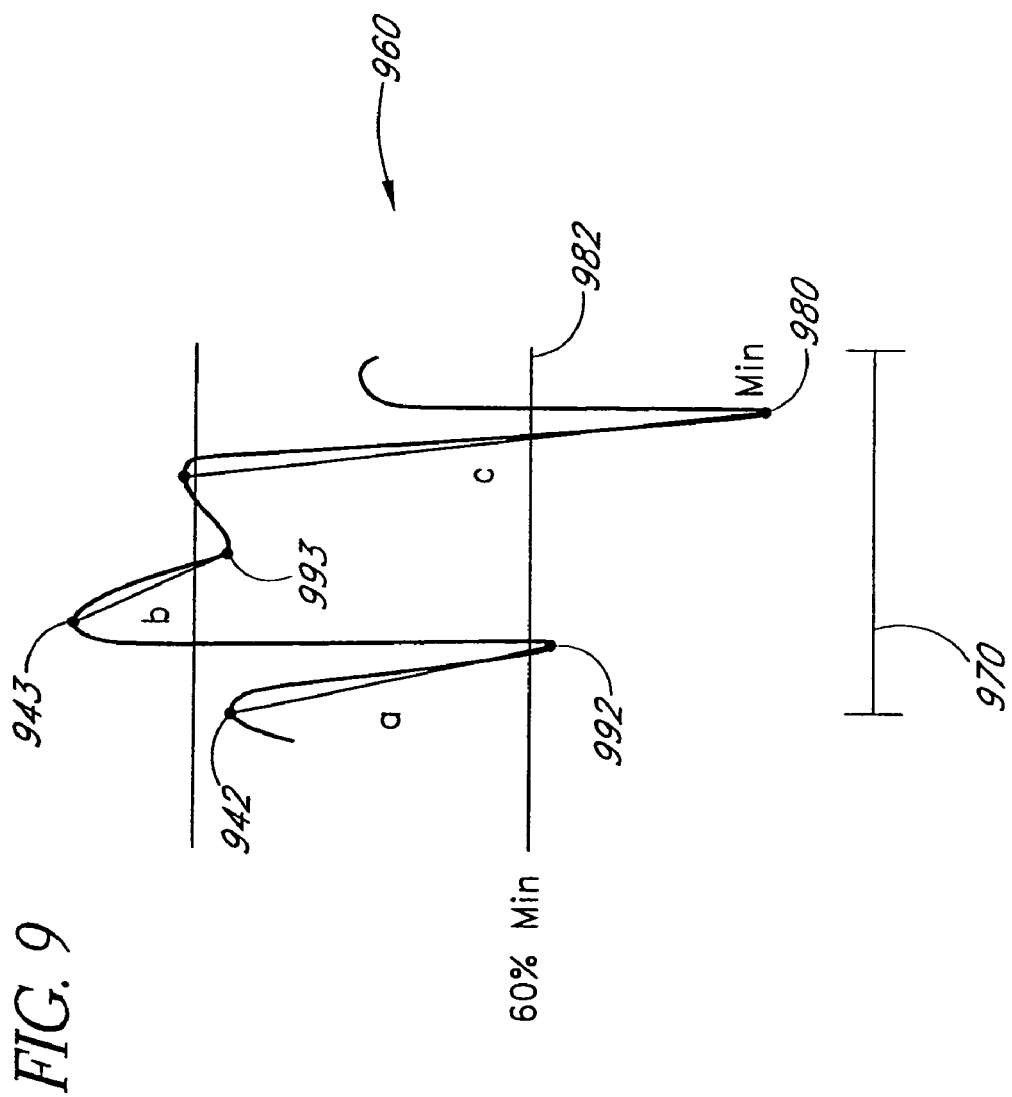
FIG. 9 is a graph illustrating the amplitude threshold check on the edges.

FIG. 9 illustrates an example of the amplitude threshold check 550 (FIG. 5). Shown is a the processed waveform 960. The starting point of the window 970 is set to the left extreme 942 (peak) of the first edge a. A minimum 980 within the window 970 is determined. A threshold 982 equal to 60% of the minimum 980 is determined. The right extreme 992 of edge a is compared with the threshold 982. Edge a is kept because the right extreme 992 is smaller than (more negative) than the threshold 982. The right extreme 993 of edge b is then compared with the threshold 982. Edge b is removed because the right extreme 993 is greater than (less negative) than the threshold 982. Similarly, edge c is kept. Next, the window 970 is moved to the left extreme 943 of edge b and the process repeated.

Also shown in FIG. 5, the max-min check 560 applies another removal criteria to the edges. The max-min check 560 considers the interval of the processed waveform between the minimum of an edge being checked and the peak of the subsequent edge. The max-min check 560 finds the maximum of the processed waveform within this interval. The edge being checked is removed if the maximum is greater than a percentage of the absolute value of the right extreme (minimum) of that edge. In one embodiment requiring the most stringent algorithm performance, the threshold is set to 77% of the right extreme of the edge. In another embodiment with less stringent algorithm performance, the threshold is set to 200% of the right extreme of the edge. The max-min check 560 is effective in eliminating edges that are pulse-like but correspond to motion.

Figure 10:
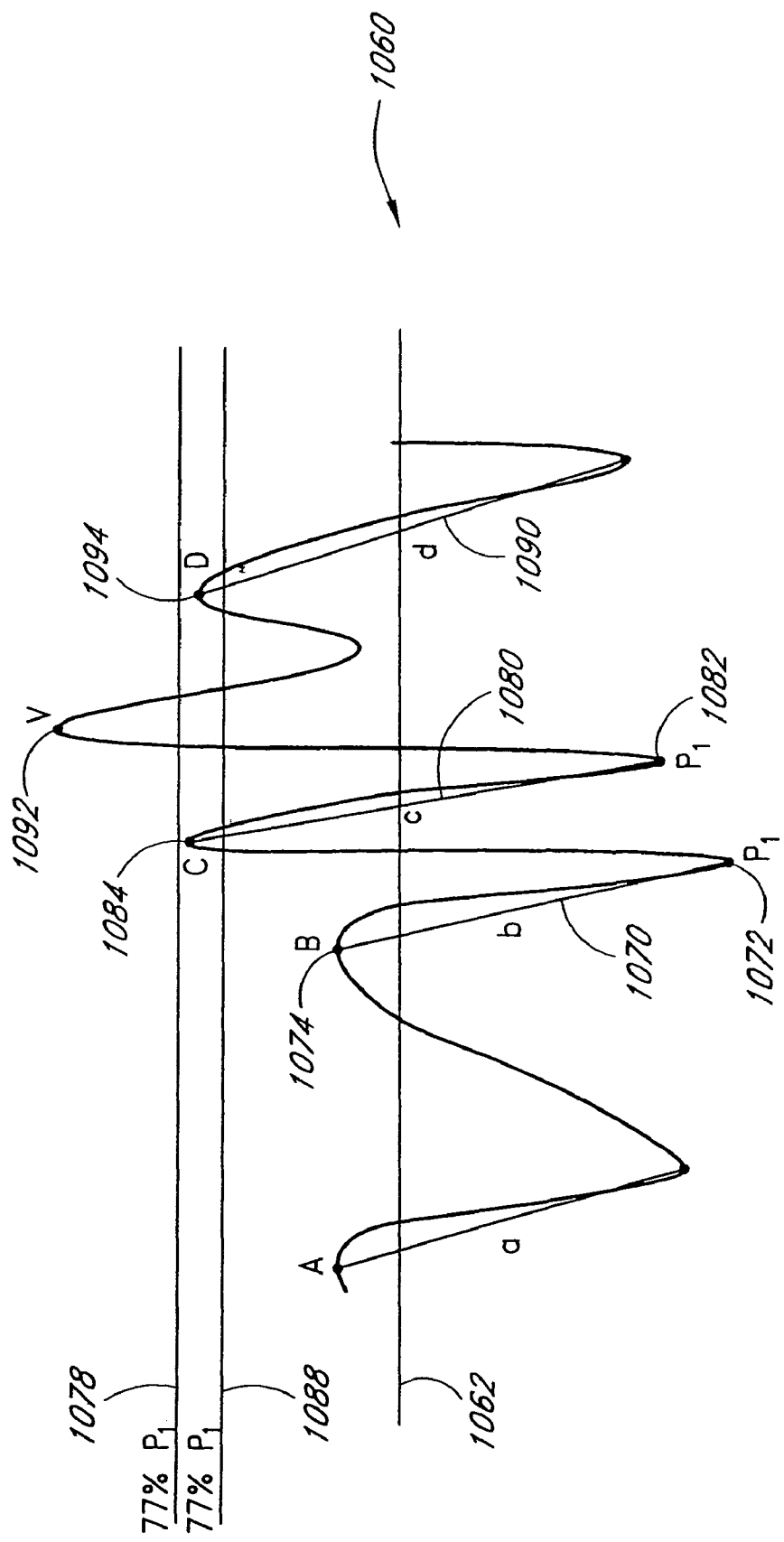
FIG. 10 is a graph illustrating the max-min check on the edges.

FIG. 10 illustrates an example of the max-min check 560 (FIG. 5). Shown is the processed waveform 1060. The max-min check 560 is applied to edge b 1070. The interval B-C is considered, which is between point B 1074, the peak of edge b 1070, and point C 1084, the peak of edge c 1080. The maximum in the interval B-C is point C 1084. Point C 1084 is compared to a first threshold 1078, which in this example is 77% of the absolute value of point P1 1072, the minimum of edge b 1070. Edge b 1070 would not be discarded because point C 1084 is smaller than this first threshold 1078. As another example, the max-min check 560 is applied to edge c 1080. The interval C-D is considered, which is between point C 1084, the peak of edge c 1080, and point D 1094, the peak of edge d 1090. The maximum in the interval C-D is point V 1093. Point V 1093 is compared to a second threshold 1088, which is 77% of the absolute value of point P2 1082, the valley of edge c 1080. Edge c would be discarded because point V 1093 is greater than this second threshold 1088.

As shown in FIG. 5, the pulse finder 570 is the last component of the candidate pulse subprocessor 410. The pulse finder 570 transforms the edges remaining after the various edge checks into candidate pulses in the form of an idealized triangular wave, which are fed into the plethysmograph model subprocessor 460 (FIG. 4). From the information about the indices of the peaks of valleys of the remaining edges, it is simple to determine a pulse in the input waveform. The remaining edges are first divided into edge pairs, i.e. the first and second edges, the second and third edges, and so on. The first point of a pulse corresponds to the maximum of the waveform segment in the interval of indices determined by the peak and valley of the first edge of a pair. The second point is the minimum between the valley of the first edge and the peak of the second edge. The third and last point is the maximum between the peak and the valley of the second edge.

Figure 11:
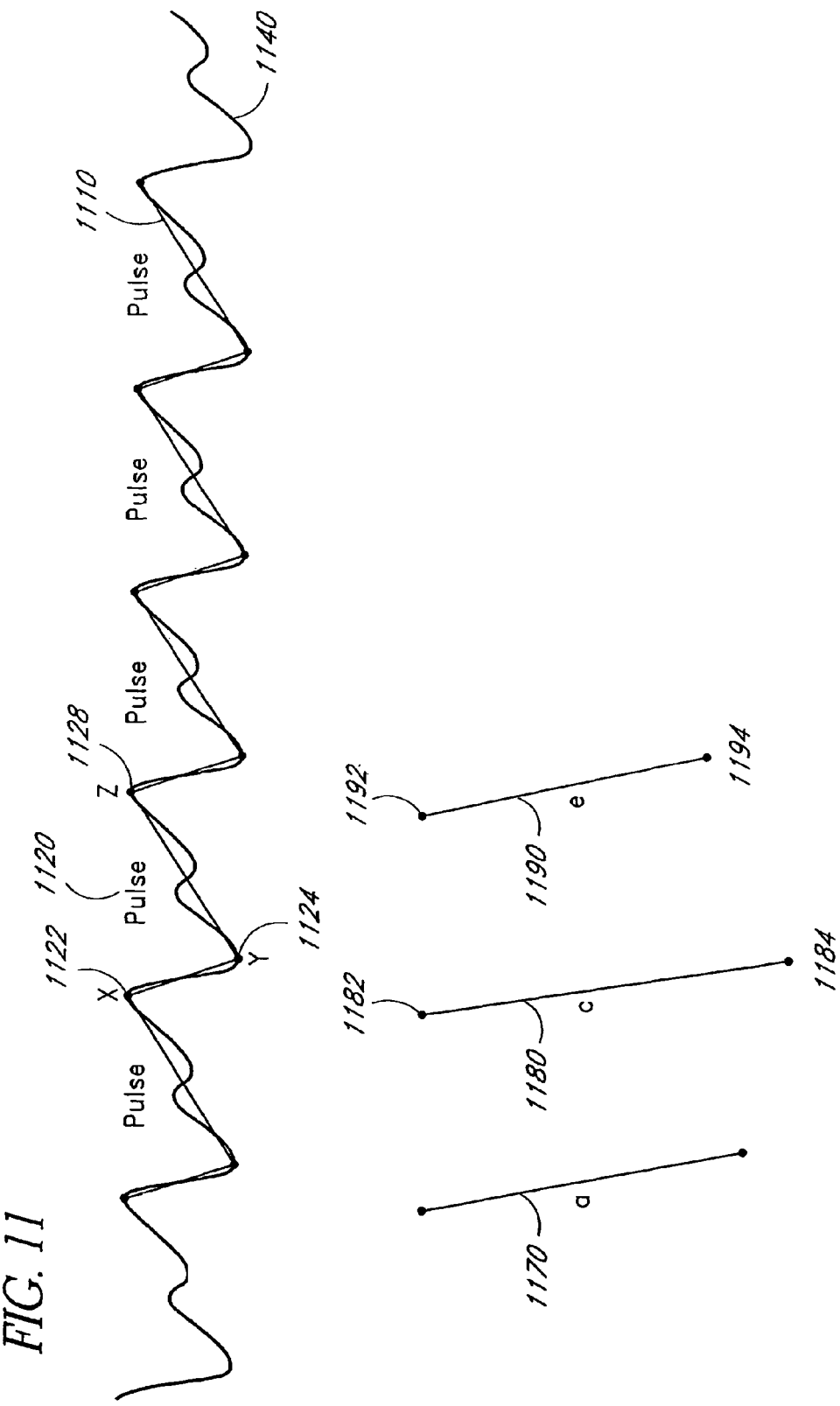
FIG. 11 is a graph illustrating the output of the pulse finder.

FIG. 11 illustrates the result of the pulse finder 570 (FIG. 5) shown as a series of pulses 1110, including a particular pulse XYZ 1120 appearing as a triangular wave superimposed on an input waveform segment 1140. Also shown are the remaining edges a 1170, b 1180 and c 1190. In this example, pulse XYZ 1120 is formed from the pair of edges c 1180 and e 1190. Point X 1122 is the maximum in the waveform segment 1140 in the time interval between the peak 1182 and valley 1184 of edge c 1180. Point Y 1124 is the minimum in the waveform segment 1140 in the time interval between the valley 1184 of edge c 1180 and the peak 1192 of edge e 1190. Point Z 1128 is the maximum in the waveform segment 1140 in the time interval between the peak 1192 and valley 1194 of edge e 1190.

Figure 12:
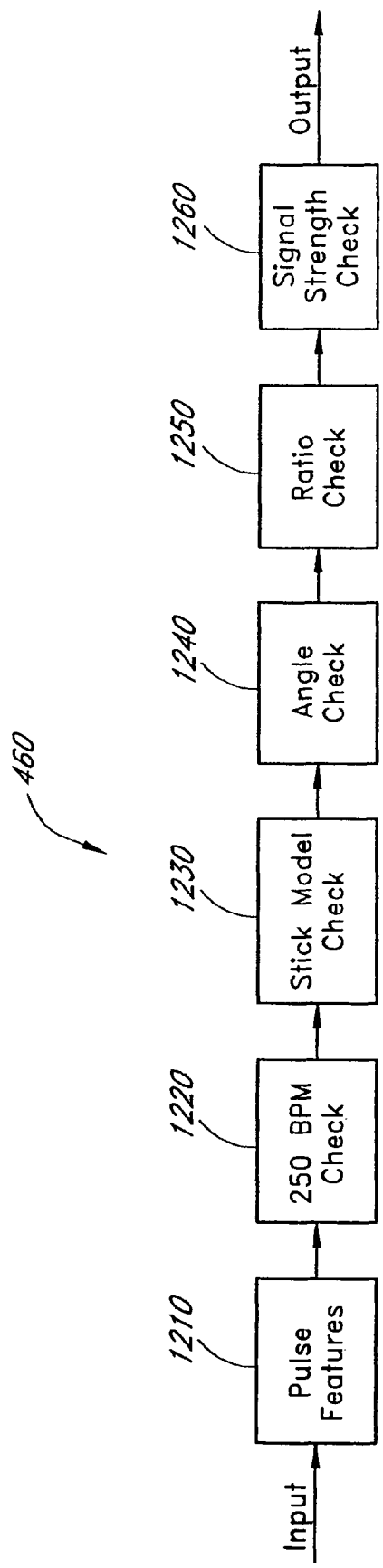
FIG. 12 is a block diagram of the plethysmograph model subprocessor portion of the present invention.

FIG. 12 illustrates the components of the plethysmograph model subprocessor 460. This subprocessor takes as input the candidate pulses identified by the candidate pulse subprocessor 410 (FIG. 4) and decides which of these satisfies an internal model for a physiological plethysmographic waveform. Although the candidate pulse subprocessor 410 (FIG. 4) performs a series of checks on edges, the plethysmograph model subprocessor performs a series of checks on pulse features. The first component of the model subprocessor calculates relevant pulse features. The remainder of the model subprocessor checks these pulse features to identify physiologically acceptable features.

Shown in FIG. 12, the pulse features component 1210 extracts three items of information about the input candidate pulses that are needed for downstream processing by the other components of the model subprocessor. The extracted features are the pulse starting point, period and signal strength.

Figure 13:
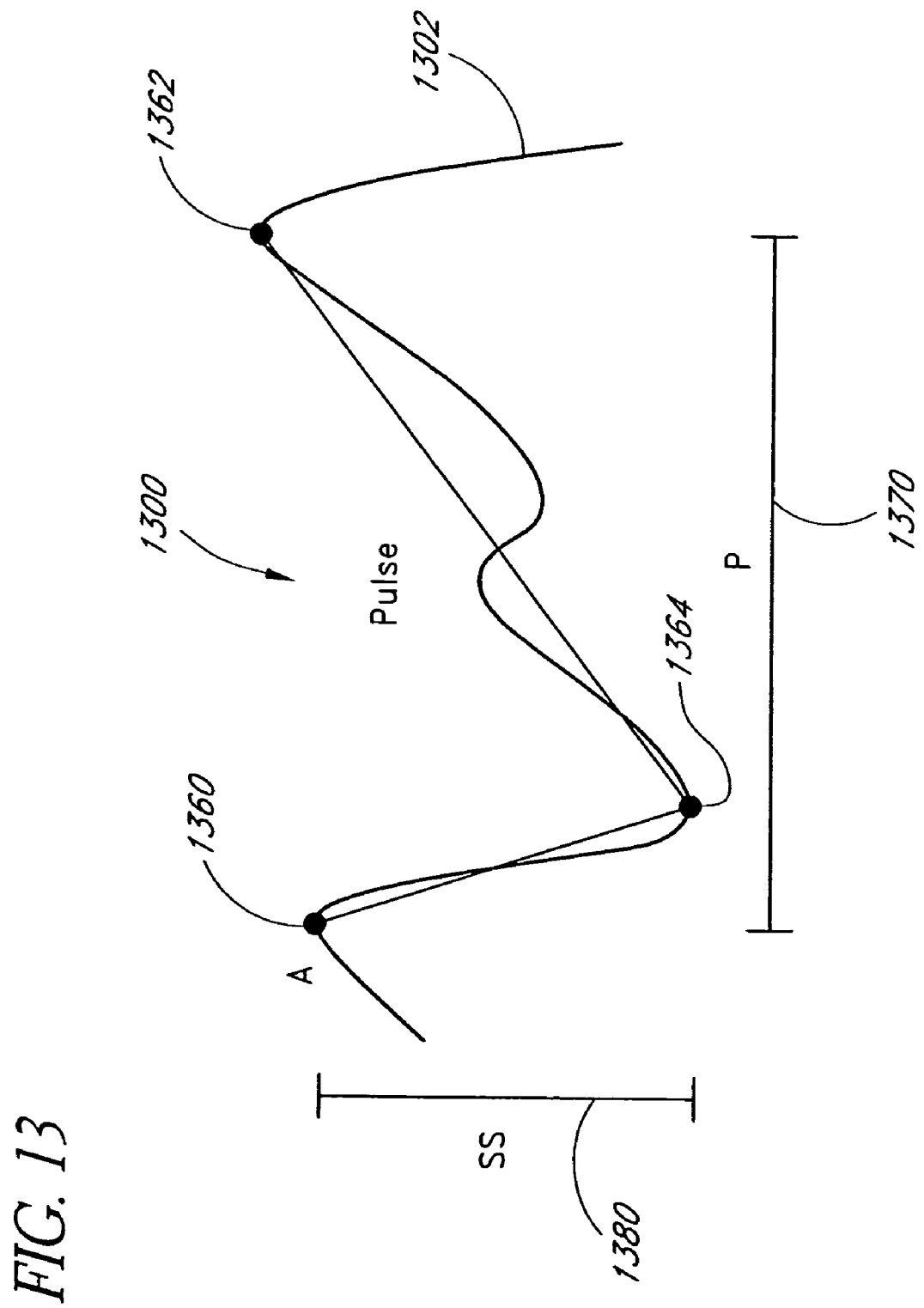
FIG. 13 is a graph illustrating the parameters extracted by the pulse features component of the model subprocessor.

FIG. 13 illustrates a candidate pulse 1300 and the three parameters extracted by the pulse features component 1210 (FIG. 12). The pulse 1300 is shown overlaid on the input waveform 1302 for reference. The starting point A 1360 is the first peak of the pulse 1300. The period P 1370 is the time difference between the time of occurrence of the first peak 1360 and the second peak 1362 of the pulse 1300. The signal strength SS 1350 is the difference between the values of the first peak 1360 and the valley 1364 of the pulse 1300. The signal strength SS 1350 is normalized by dividing this value by the value of the infrared raw signal data at the point corresponding to point A 1360.

Also shown in FIG. 12 is the 250 BPM check 1220. This component discards pulses having a period P 1370 (FIG. 13) that is below 15 samples. This corresponds to an upper limit for the pulse rate set at 250 beats per minute. That is:

$$15 \text{ samples/beat} = (62.5 \text{ samples/sec.} \times 60 \text{ sec./min.})/250 \text{ beats per min} \quad (2)$$

In addition, FIG. 12 shows the stick model check 1230. This component discards pulses where the corresponding waveform does not closely fit a stick model, i.e. where a pulse cannot be represented by a triangular waveform. This component measures a normalized difference between the input waveform and the triangular wave representation of that waveform. The obtained value is compared to a threshold, and pulses are discarded where the normalized difference is greater than that threshold.

Figure 14:
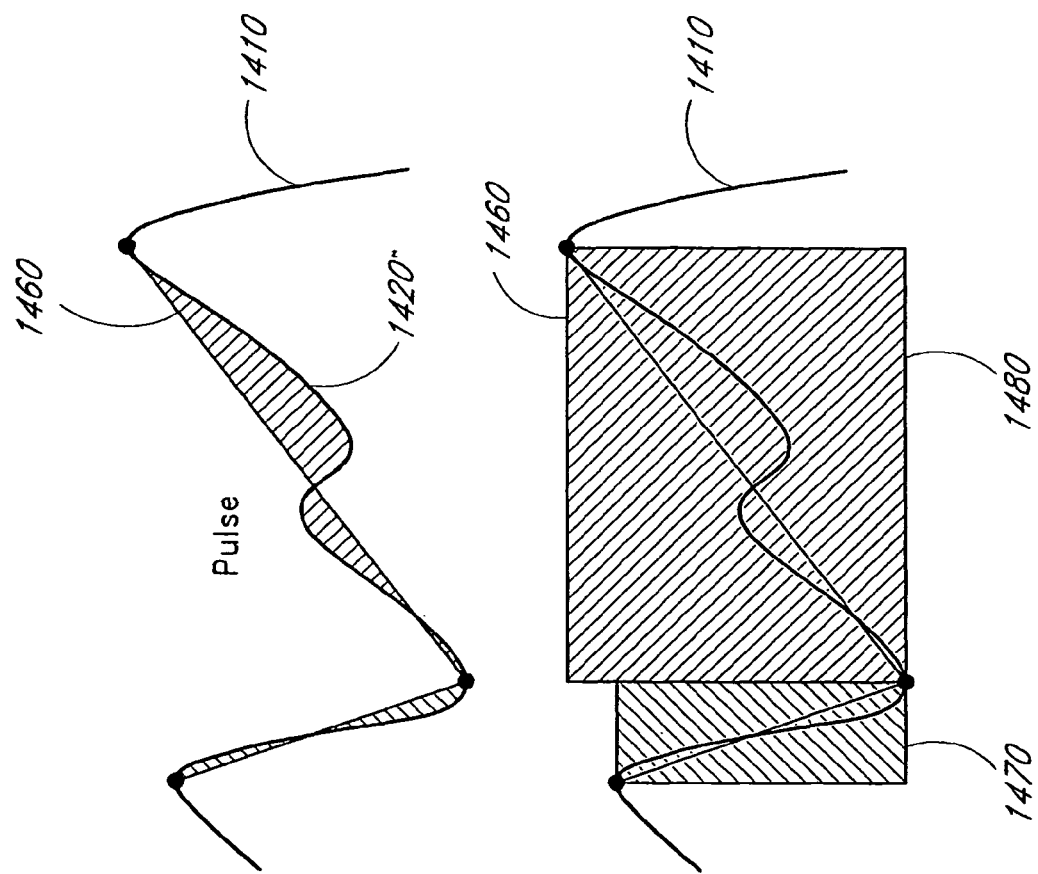
FIG. 14 is a graph illustrating the stick model check on the candidate pulses.

FIG. 14 illustrates the calculations performed by the stick model check 1230 (FIG. 12). Shown is an input waveform pulse 1410 and the corresponding stick model pulse 1460. The stick model check 1230 (FIG. 12) component computes a first value, which is a sum of the absolute differences, shown as the dark black areas 1420, between the waveform pulse 1410 and the stick model pulse 1460. This component also computes a second value, which is a sum of the first rectangular gray area 1470 enclosing the descending portion of the pulse 1410 and the second gray area 1480 enclosing the ascending portion of the pulse 1410. The stick model check 1230 (FIG. 12) then normalizes the first value by dividing it by the second value. This normalized value is compared with a threshold. A physiological pulse does not differ too much from the stick model at high pulse rates. This is not true at pulse rates much below 150 bpm because of the appearance of a dicrotic notch and other "bumps." Hence, the threshold is a function of pulse rate. In one embodiment, the threshold is:

| | | |
|---|---|---|
| 0.15, | for pulse rate < 130 | (3) |
| $0.430455769 e^{-0.008109302}$(pulse rate), | for 130 < pulse rate < 160 | (4) |
| 0.1, | for pulse rate > 160 | (5) |

Shown in FIG. 12 is the angle check 1240. The angle check 1240 is based on computing the angle of a normalized slope for the ascending portion of a pulse. This angle is compared with the same angle of an ideal pulse having the same period. This check is effective in discarding pulses that are extremely asymmetric.

Figure 15:
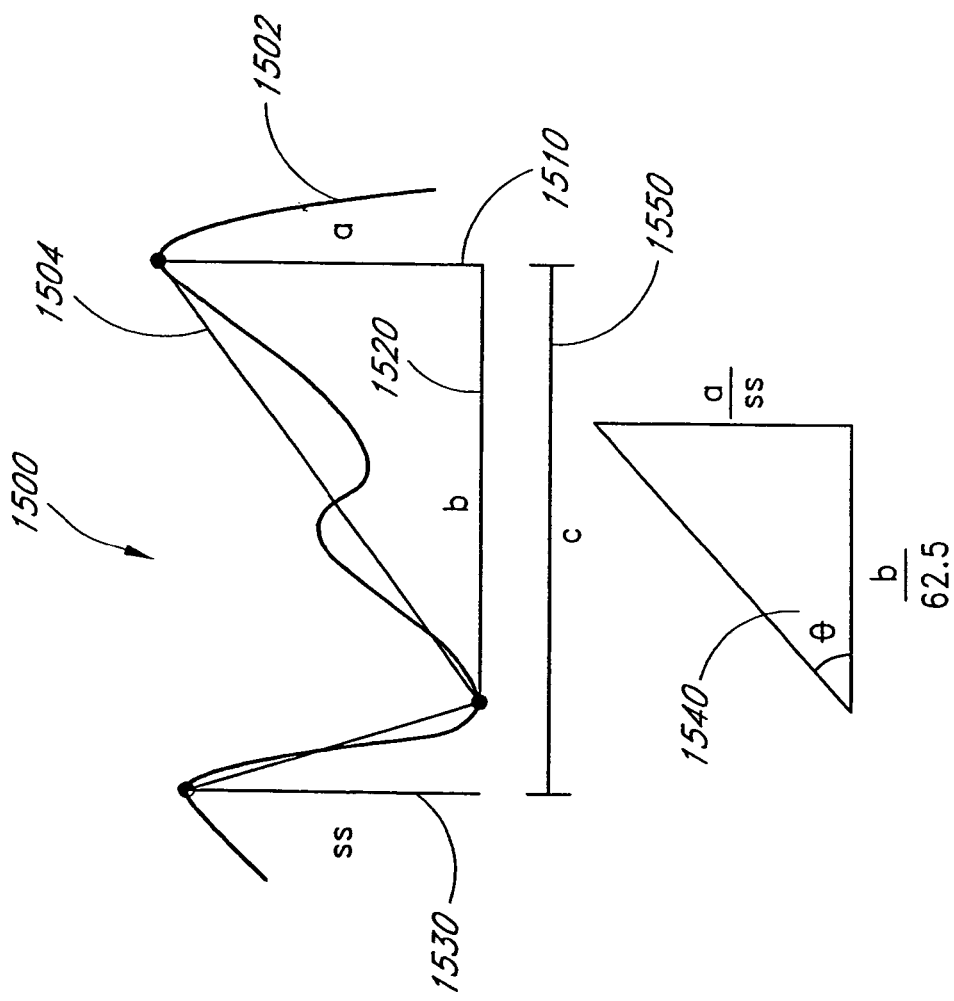
FIG. 15 is a graph illustrating an angle check on the candidate pulses.

FIG. 15 illustrates an example of the angle check 1240 (FIG. 12). Shown is a single triangular pulse 1500 superimposed on the corresponding input waveform 1502. The ascending pulse portion 1504 has a vertical rise a 1510 and a horizontal run b 1520. The rise 1510 and run 1520 are normalized with respect to the pulse signal strength ss 1530 and the pulse frequency, which is 62.5 Hz. in this particular embodiment. An angle θ 1540 is computed as:

$$\theta = \arctan\left[(a/ss)/(b/62.5)\right] \times 180/\pi \quad (6)$$

The angle θ is compared with the same angle of an ideal pulse having the same period, where a is equal to the signal strength and b is equal to the period c 1550 minus 6. Three degrees are added to this value as a threshold margin. Hence, θ is compared to $\theta_{ref}$ computed as follow:

$$\theta_{ref} = \arctan\left\{[a/ss]/[(c-6)/62.5]\right\} \times (180/\pi) + 3 \quad (7)$$

Figure 16:
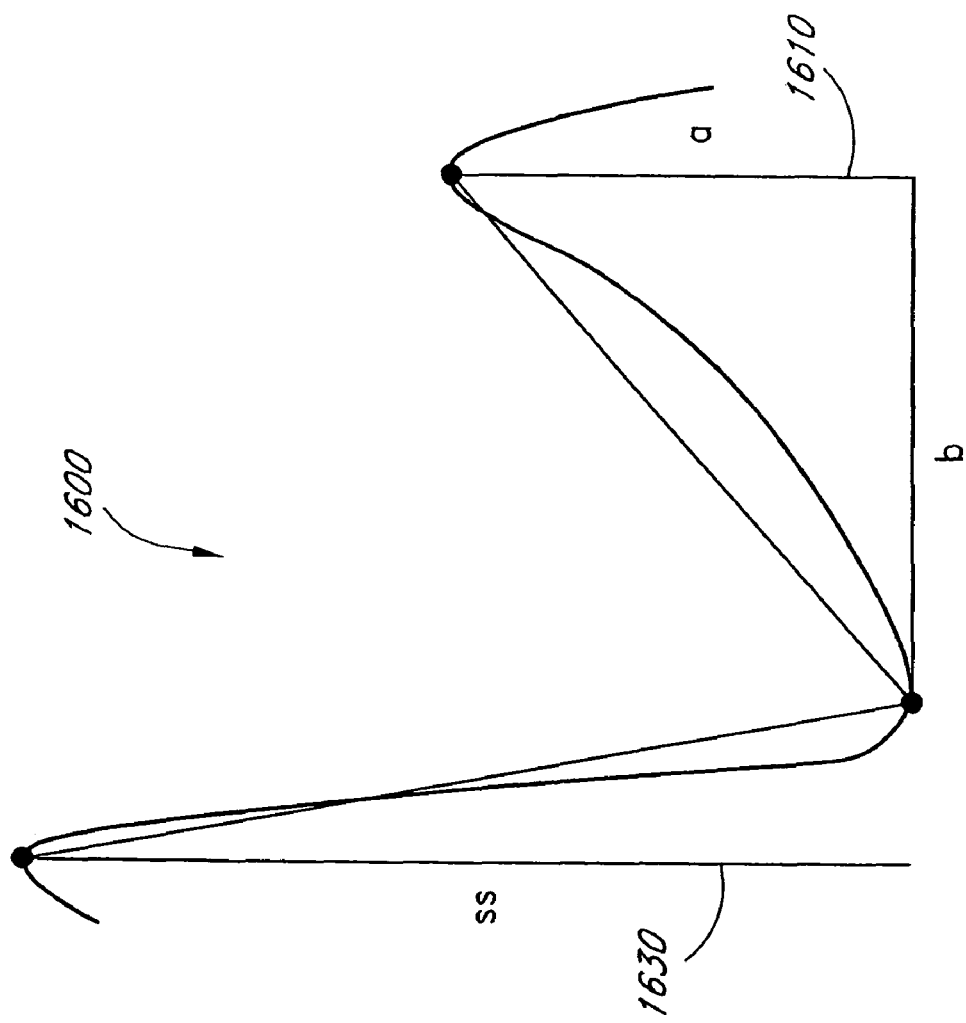
FIG. 16 is a graph illustrating a pulse that would be discarded by the angle check.

If $\theta < \theta_{ref}$, then the pulse is discarded. FIG. 16 illustrates an example pulse 1600 that would be discarded by the angle check, because the segment a 1610 is much smaller than the signal strength ss 1630.

Also shown in FIG. 12 is the ratio check 1250. The time ratio check component removes pulses in which the ratio between the duration of the ascending pulse portion and the duration of the descending pulse portion is less than a certain threshold. In a particular embodiment, the threshold is 1.1. The rationale for this check is that in every physiological pulse the ascending portion is shorter in time than the descending portion, which represents the ventricular contraction.

Figure 17:
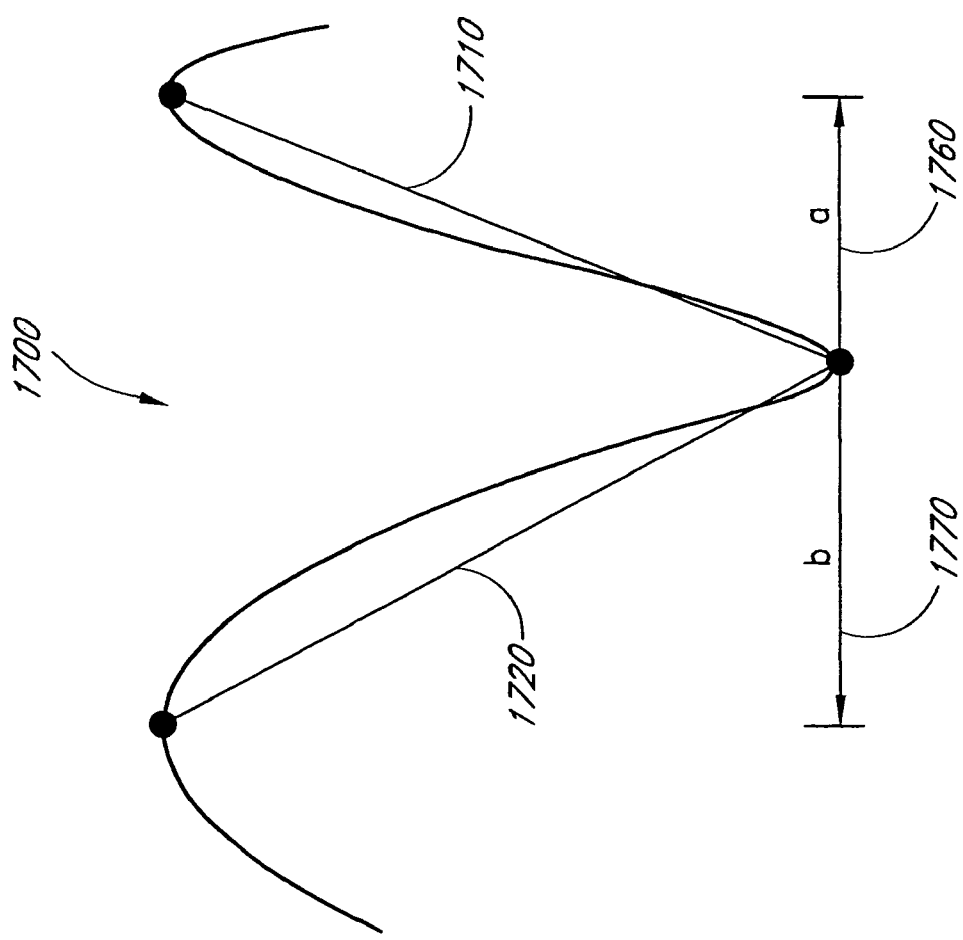
FIG. 17 is a graph illustrating a pulse that would be discarded by the ratio check.

FIG. 17 illustrates an example pulse 1700 that would be discarded by the time ratio check 1250 (FIG. 12). In this example, the duration a 1760 of the ascending portion 1710 is less than the duration b 1770 of the descending portion 1720. Hence, the ratio of the ascending duration 1760 to the descending duration 1770, a/b, is less than the threshold 1.1.

FIG. 12 further shows the signal strength check 1260. The signal strength check 1260 assigns a confidence value to each pulse, based on its signal strength. There are two levels of confidence, high and low. The determination of confidence is based on two mechanisms. The first mechanism is founded on the observation that the higher the pulse rate, the lower the signal strength. This mechanism is implemented with an empirical relationship between pulse rate and signal strength. If the measured signal strength is greater than this empirical relationship by a fixed margin, the pulse confidence is low. The second mechanism incorporates the physiological limitation that signal strength cannot change too much over a short period of time. If the pulse signal strength is greater than a short-term average signal strength by a fixed margin, the pulse confidence is low. If the pulse meets both criteria, then the pulse has a high confidence. All pulses in a single waveform segment or snapshot have the same confidence value. Hence, if there is a least one pulse with a high confidence, then all pulses with a low confidence will be dropped.

Figure 18:
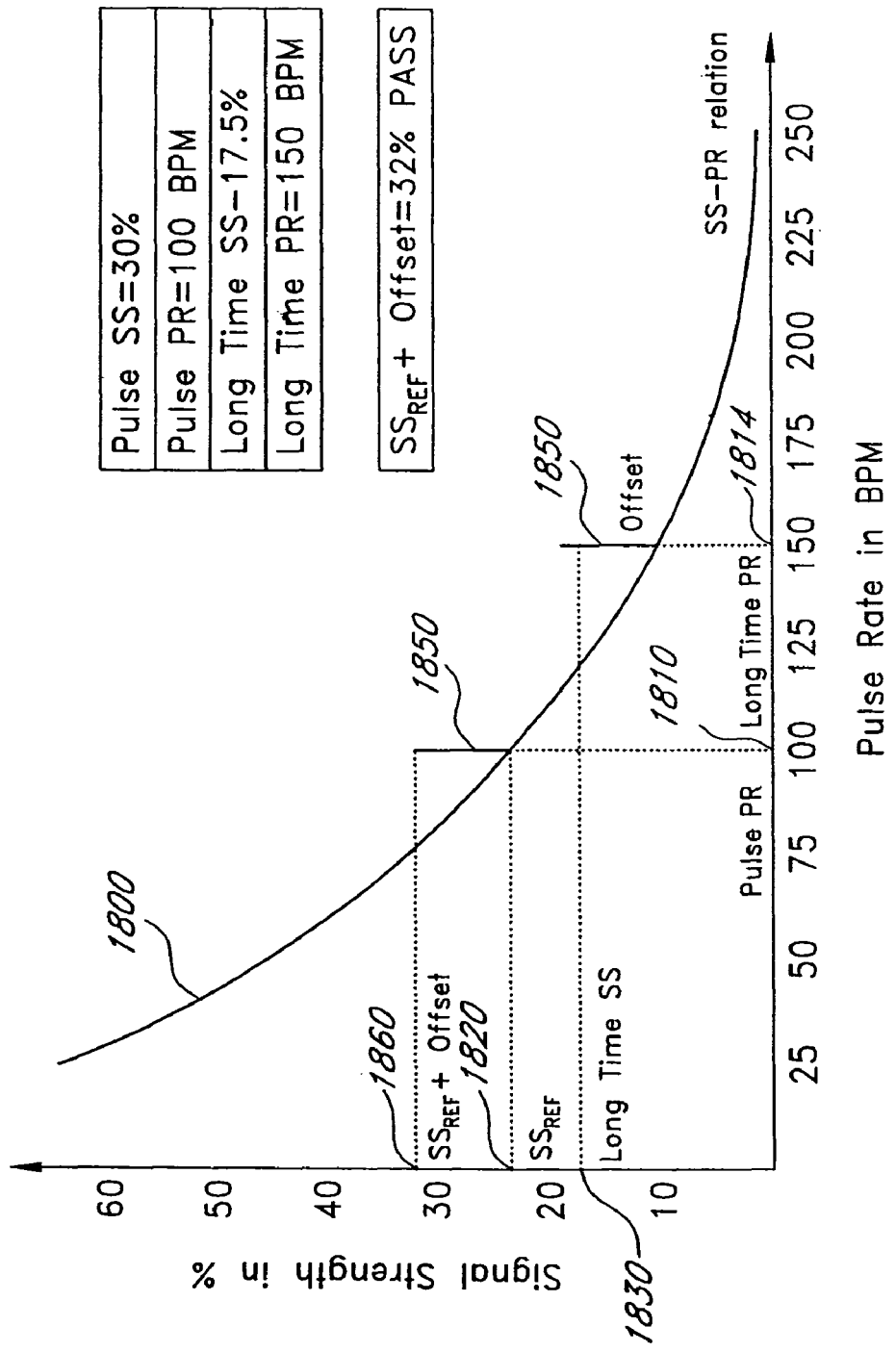
FIG. 18 is a graph illustrating one test of the signal strength check.

FIG. 18 illustrates the first signal strength criteria described above. In one embodiment, the relationship between signal strength and pulse rate is given by curve 1800, which is described by the following equation:

$$SS = 110 \cdot e^{-0.02131 PR} + 1 \qquad (8)$$

First, the pulse rate, PR 1810, is determined from the pulse period. Next, the corresponding signal strength, $SS_{ref}$ 1820, is determined from equation (8) and the pulse rate 1810. Because equation (8) is empirically derived, it is shifted up and down to make it more applicable for individual patients. A long-term average signal strength, Long Time SS 1830, and a long-term average pulse rate, Long Time PR 1840, are derived. If Long Time SS 1830 is above the curve 1800 at the point corresponding to the Long Time PR 1840, then the difference between the Long Time SS and the curve 1800 plus 2 becomes Offset 1850. If the measured pulse signal strength, Pulse SS, is less than $SS_{ref}$+Offset 1860, then this check is passed.

As shown in FIG. 4, after the candidate pulse subprocessor 410 and the plethysmograph model subprocessor 460, the pulse recognition processor 400 has identified inside the input waveform snapshot all of the pulses that meet a certain model for physiologically acceptable plethysmographs. From the information about these pulses, the pulse statistics subprocessor 490 can extract statistics regarding the snapshot itself. Two useful statistical parameters that are derived are the median value of the pulse periods and signal strengths. The median is used rather than the mean because inside a waveform snapshot of 400 points (almost 7 seconds) the period and signal strength associated with each pulse can vary widely. Another parameter is the signal strength confidence level, which in one embodiment is the same for all the recognized pulses of a snapshot. A fourth useful parameter is pulse density. Pulse density is the value obtained by dividing the sum of the periods of the acceptable pulses by the length of the snapshot. Pulse density represents that ratio of the snapshot that has been classified as physiologically acceptable. Pulse density is a value between 0 and 1, where 1 means that all of the snapshot is physiologically acceptable. In other words, pulse density is a measure of whether the data is clean or distorted, for example by motion artifact.

Figure 19:
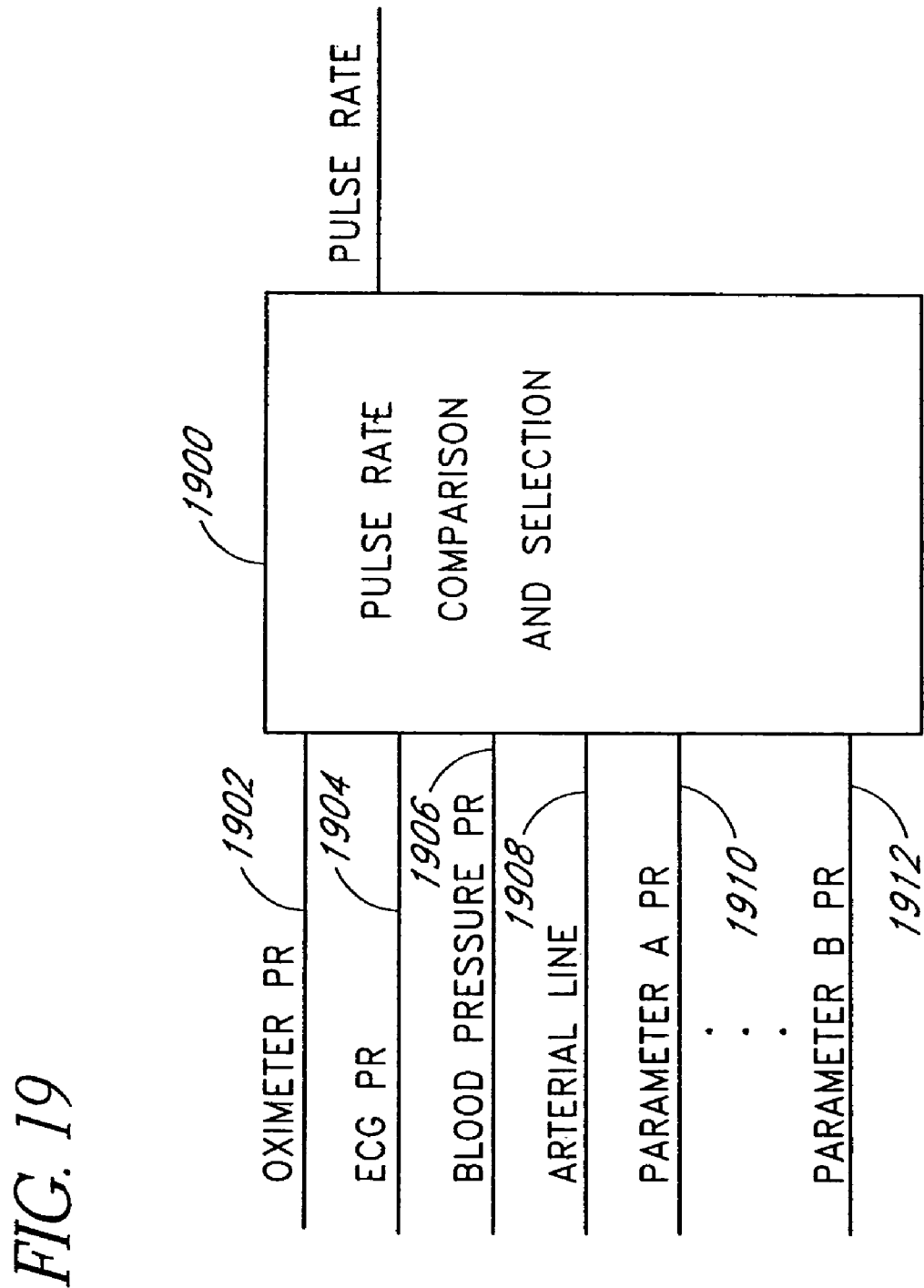
FIG. 19 is a block diagram of a pulse rate selection and comparison module in accordance with a preferred embodiment of the present invention.

Finally, based on these described criteria, a pulse rate may be chosen. In a system with additional monitoring inputs, as depicted in FIG. 19, a pulse rate selection and comparison module 1900 may be provided. For example, the oximeter pulse rate (and corresponding confidence information if desired) can be provided on a first input 1902. In a multiparameter patient monitor, there may also be pulse rate or pulse information (and possibly confidence information) from an ECG or EKG monitor on a second input 1904, from a blood pressure monitor on a third input 1906, from an arterial line on a fourth input 1908, and other possible parameters 1910, 1912. The pulse rate module 1900 then compares the various inputs, and can determine which correlate or which correlate and have the highest confidence association. The selected pulse rate is then provided on an output 1914. Alternatively, the pulse rate module 1900 may average each input, a selection of the inputs or provide a weighted average based on confidence information if available.

The plethysmograph pulse recognition processor has been disclosed in detail in connection with various embodiments of the present invention. These embodiments are disclosed by way of examples only and are not to limit the scope of the present invention, which is defined by the claims that follow. One of ordinary skill in the art will appreciate many variations and modifications within the scope of this invention.

What is claimed is:

1. A patient monitor comprising:
   an input which receives a sensor signal indicative of light attenuated by body tissue; and
   a processor which applies a plurality of first edge analysis rules to identify potential pulses from within said sensor signal or from within signals derived from said sensor signal, the processor also applying a plurality of second pulse feature rules to identify acceptable pulses from within said potential pulses, wherein said plurality of said second rules comprise at least one signal modeling rule.

2. The monitor of claim 1, wherein the processor determines statistical pulse rate information from said acceptable pulses.

3. The monitor of claim 2, wherein said statistical pulse rate information comprises pulse period information.

4. The monitor of claim 2, wherein said statistical pulse rate information comprises pulse density information.

5. The monitor of claim 1, wherein said at least one signal modeling rule determines a difference between at least one signal model and said potential pulses.

6. The monitor of claim 5, wherein where said at least one signal modeling rule varies acceptable threshold values to be compared to said difference.

7. The monitor of claim 6, wherein said varying is pulse dependent.

8. The monitor of claim 7, wherein signal features of said potential pulses change when said pulse changes.

9. The monitor of claim 6, wherein said varying accounts for effects of a rising pulse rate on said potential pulses.

10. The monitor of claim 1, wherein the pulse feature rules relate to a pulse starting point.

11. The monitor of claim 1, wherein the pulse feature rules relate to a period.

12. The monitor of claim 1, wherein the pulse feature rules relate to a signal strength.

* * * * *

UNITED STATES PATENT AND TRADEMARK OFFICE
CERTIFICATE OF CORRECTION

| | | |
|---|---|---|
| PATENT NO. | : 7,988,637 B2 | |
| APPLICATION NO. | : 11/418328 | |
| DATED | : August 2, 2011 | |
| INVENTOR(S) | : Mohamed K. Diab | |

It is certified that error appears in the above-identified patent and that said Letters Patent is hereby corrected as shown below:

At column 5, line 58, please delete "is a the" and insert therefore, --is the--.

At column 10, line 37, please delete "wherein where said" and insert therefore, --wherein said--.

Signed and Sealed this
Twenty-first Day of February, 2012

David J. Kappos
*Director of the United States Patent and Trademark Office*